(12) United States Patent
Layman et al.

(10) Patent No.: US 8,142,619 B2
(45) Date of Patent: Mar. 27, 2012

(54) SHAPE OF CONE AND AIR INPUT ANNULUS

(75) Inventors: Frederick P. Layman, Carefree, AZ (US); Maximilian A. Biberger, Scottsdale, AZ (US)

(73) Assignee: SDC Materials Inc., Tempe, AZ (US)

( * ) Notice: Subject to any disclaimer, the term of this patent is extended or adjusted under 35 U.S.C. 154(b) by 391 days.

(21) Appl. No.: 12/151,766

(22) Filed: May 8, 2008

(65) Prior Publication Data

US 2008/0277266 A1    Nov. 13, 2008

Related U.S. Application Data

(60) Provisional application No. 60/928,946, filed on May 11, 2007.

(51) Int. Cl.
| | |
|---|---|
| C07C 1/00 | (2006.01) |
| B01J 19/08 | (2006.01) |
| B22F 9/00 | (2006.01) |
| B22F 9/14 | (2006.01) |

(52) U.S. Cl. ............... 204/157.15; 422/186.04; 422/186; 75/332; 75/346

(58) Field of Classification Search ............. 204/157.15; 75/332, 346; 422/186.04, 186
See application file for complete search history.

(56) References Cited

U.S. PATENT DOCUMENTS

| | | | |
|---|---|---|---|
| 2,284,554 A | 5/1942 | Beyerstedt | |
| 2,419,042 A | 4/1947 | Todd | 202/205 |
| 2,519,531 A | 8/1950 | Worn | 230/95 |
| 2,562,753 A * | 7/1951 | Trost | 241/39 |
| 2,689,780 A | 9/1954 | Rice | 23/106 |
| 3,001,402 A | 9/1961 | Koblin | 73/421.5 |
| 3,067,025 A * | 12/1962 | Chisholm | 75/616 |
| 3,145,287 A | 8/1964 | Siebein et al. | |
| 3,178,121 A * | 4/1965 | Wallace, Jr. | 241/5 |

(Continued)

FOREIGN PATENT DOCUMENTS

JP    56-146804    11/1981

(Continued)

OTHER PUBLICATIONS

Kenvin et al. "Supported Catalysts Prepared from Monouclear Copper Complexes: Catalytic Properties", Journal of Catalysis, pp. 81-91.

(Continued)

*Primary Examiner* — Keith Hendricks
*Assistant Examiner* — Colleen M Raphael
(74) *Attorney, Agent, or Firm* — Haverstock & Owens LLP

(57) ABSTRACT

A constricting chamber having first and second ends, the chamber comprising: an interior surface formed between the first and second ends, disposed circumferentially around and defining an interior space and a longitudinal axis of the chamber; a frusto-conical surface disposed between the first and second ends and narrowing as it extends away from the first end and into the second end; an ejection port disposed at the second end and substantially aligned with the longitudinal axis; a cover disposed at the first end, substantially perpendicular to the longitudinal axis, and comprising a center substantially aligned with the longitudinal axis; an injection port disposed on the cover proximate the center, and configured to receive a reactive mixture into the chamber; and an annular supply portion disposed circumferentially around the longitudinal axis and comprising supply port(s) configured to supply conditioning fluid into the chamber in an annular formation along the interior surface.

11 Claims, 5 Drawing Sheets

U.S. PATENT DOCUMENTS

| | | | |
|---|---|---|---|
| 3,179,782 A | 4/1965 | Matvay | |
| 3,313,908 A | 4/1967 | Unger et al. | |
| 3,401,465 A * | 9/1968 | Larwill | 34/586 |
| 3,450,926 A * | 6/1969 | Kiernan | 219/121.49 |
| 3,457,788 A | 7/1969 | Miyajima | 73/422 |
| 3,537,513 A | 11/1970 | Austin et al. | 165/70 |
| 3,741,001 A | 6/1973 | Fletcher et al. | 73/28 |
| 3,752,172 A * | 8/1973 | Cohen et al. | 137/12 |
| 3,774,442 A | 11/1973 | Gustavsson | 73/28 |
| 3,830,756 A | 8/1974 | Sanchez et al. | |
| 3,892,882 A | 7/1975 | Guest et al. | |
| 3,914,573 A | 10/1975 | Muehlberger | |
| 3,959,420 A | 5/1976 | Geddes et al. | 261/112 |
| 4,008,620 A | 2/1977 | Narato et al. | 73/421.5 A |
| 4,018,388 A * | 4/1977 | Andrews | 241/39 |
| 4,139,497 A | 2/1979 | Castor et al. | |
| 4,157,316 A | 6/1979 | Thompson et al. | |
| 4,171,288 A | 10/1979 | Keith et al. | |
| 4,174,298 A | 11/1979 | Antos | |
| 4,248,387 A * | 2/1981 | Andrews | 241/5 |
| 4,284,609 A | 8/1981 | deVries | |
| 4,388,274 A | 6/1983 | Rourke et al. | |
| 4,431,750 A | 2/1984 | McGinnis et al. | |
| 4,436,075 A | 3/1984 | Campbell et al. | 123/557 |
| 4,505,945 A | 3/1985 | Dubust et al. | |
| 4,513,149 A | 4/1985 | Gray et al. | |
| 4,731,517 A | 3/1988 | Cheney | |
| 4,764,283 A * | 8/1988 | Ashbrook et al. | 210/695 |
| 4,824,624 A | 4/1989 | Palicka et al. | 264/67 |
| 4,855,505 A | 8/1989 | Koll | |
| 4,866,240 A | 9/1989 | Webber | |
| 4,983,555 A | 1/1991 | Roy et al. | 501/120 |
| 4,987,033 A | 1/1991 | Abkowitz et al. | 428/469 |
| 5,041,713 A | 8/1991 | Weidman | |
| 5,043,548 A | 8/1991 | Whitney et al. | 219/121.84 |
| 5,070,064 A | 12/1991 | Hsu et al. | |
| 5,073,193 A * | 12/1991 | Chaklader et al. | 75/346 |
| 5,157,007 A | 10/1992 | Domesle et al. | |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,439,865 A | 8/1995 | Abe et al. | |
| 5,442,153 A | 8/1995 | Marantz et al. | |
| 5,460,701 A | 10/1995 | Parker et al. | |
| 5,485,941 A | 1/1996 | Guyomard et al. | 222/1 |
| 5,534,149 A | 7/1996 | Birkenbeil et al. | |
| 5,553,507 A | 9/1996 | Basch et al. | 73/863.01 |
| 5,611,896 A | 3/1997 | Swanepoel et al. | 204/169 |
| 5,630,322 A | 5/1997 | Heilmann et al. | 62/95 |
| 5,726,414 A | 3/1998 | Kitahashi et al. | |
| 5,749,938 A * | 5/1998 | Coombs | 75/332 |
| 5,776,359 A | 7/1998 | Schultz et al. | 252/62.51 |
| 5,788,738 A * | 8/1998 | Pirzada et al. | 75/331 |
| 5,811,187 A | 9/1998 | Anderson et al. | 428/403 |
| 5,837,959 A | 11/1998 | Muehlberger et al. | |
| 5,851,507 A * | 12/1998 | Pirzada et al. | 423/659 |
| 5,853,815 A | 12/1998 | Muehlberger | 427/446 |
| 5,905,000 A | 5/1999 | Yadav et al. | 429/33 |
| 5,935,293 A | 8/1999 | Detering et al. | 75/10.29 |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,012,647 A | 1/2000 | Ruta et al. | 239/132.1 |
| 6,033,781 A | 3/2000 | Brotzman, Jr. et al. | 428/405 |
| 6,059,853 A | 5/2000 | Coombs | 75/332 |
| 6,102,106 A | 8/2000 | Manning et al. | 165/76 |
| 6,213,049 B1 | 4/2001 | Yang | |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,342,465 B1 | 1/2002 | Klein et al. | |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 | 7/2002 | Geis et al. | |
| 6,416,818 B1 | 7/2002 | Aikens et al. | 427/383.1 |
| RE37,853 E | 9/2002 | Detering et al. | 75/10.19 |
| 6,444,009 B1 * | 9/2002 | Liu et al. | 75/332 |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | |
| 6,554,609 B2 | 4/2003 | Yadav et al. | 432/9 |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,596,187 B2 | 7/2003 | Coll et al. | |
| 6,603,038 B1 | 8/2003 | Hagemeyer et al. | |
| 6,607,821 B2 | 8/2003 | Yadav et al. | 428/323 |
| 6,610,355 B2 | 8/2003 | Yadav et al. | 427/115 |
| 6,623,559 B2 * | 9/2003 | Huang | 977/775 |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,710,207 B2 | 3/2004 | Bogan, Jr. et al. | |
| 6,713,176 B2 | 3/2004 | Yadav et al. | 428/402 |
| 6,716,525 B1 | 4/2004 | Yadav et al. | 428/402 |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,527 B2 | 7/2005 | Boulos et al. | 219/121.52 |
| 6,933,331 B2 | 8/2005 | Yadav et al. | 523/210 |
| 6,986,877 B2 | 1/2006 | Takikawa et al. | 423/447.3 |
| 6,994,837 B2 * | 2/2006 | Boulos et al. | 423/613 |
| 7,007,872 B2 | 3/2006 | Yadav et al. | 241/1 |
| 7,022,305 B2 | 4/2006 | Drumm et al. | |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | |
| 7,307,195 B2 | 12/2007 | Polverejan et al. | 585/443 |
| 7,323,655 B2 * | 1/2008 | Kim | 219/121.43 |
| 7,384,447 B2 | 6/2008 | Kodas et al. | 75/332 |
| 7,417,008 B2 | 8/2008 | Richards et al. | |
| 7,494,527 B2 * | 2/2009 | Jurewicz et al. | 75/346 |
| 7,541,012 B2 | 6/2009 | Yeung et al. | |
| 7,572,315 B2 * | 8/2009 | Boulos et al. | 75/336 |
| 7,611,686 B2 | 11/2009 | Alekseeva et al. | |
| 7,615,097 B2 * | 11/2009 | McKechnie et al. | 75/346 |
| 7,622,693 B2 * | 11/2009 | Foret | 219/121.43 |
| 7,803,210 B2 | 9/2010 | Sekine et al. | |
| 2001/0042802 A1 * | 11/2001 | Youds | 241/5 |
| 2002/0068026 A1 | 6/2002 | Murrell et al. | |

| | | | |
|---|---|---|---|
| 2002/0079620 A1* | 6/2002 | Dubuis et al. | 264/328.14 |
| 2003/0036786 A1 | 2/2003 | Duren et al. | 607/96 |
| 2003/0042232 A1 | 3/2003 | Shimazu | |
| 2003/0066800 A1 | 4/2003 | Saim et al. | |
| 2003/0108459 A1* | 6/2003 | Wu et al. | 422/186.04 |
| 2003/0139288 A1 | 7/2003 | Cai et al. | |
| 2003/0172772 A1 | 9/2003 | Sethuram et al. | |
| 2003/0223546 A1 | 12/2003 | McGregor et al. | 378/143 |
| 2004/0009118 A1 | 1/2004 | Phillips et al. | |
| 2004/0023302 A1 | 2/2004 | Archibald et al. | |
| 2004/0023453 A1 | 2/2004 | Xu et al. | |
| 2004/0103751 A1 | 6/2004 | Joseph et al. | 75/10.19 |
| 2004/0119064 A1 | 6/2004 | Narayan et al. | |
| 2004/0127586 A1 | 7/2004 | Jin et al. | |
| 2004/0167009 A1 | 8/2004 | Kuntz et al. | 501/95.2 |
| 2004/0176246 A1 | 9/2004 | Shirk et al. | |
| 2004/0213998 A1 | 10/2004 | Hearley et al. | |
| 2004/0251017 A1 | 12/2004 | Pillion et al. | 165/289 |
| 2005/0000321 A1 | 1/2005 | O'Larey et al. | 75/952 |
| 2005/0000950 A1* | 1/2005 | Schroder et al. | 219/121.59 |
| 2005/0077034 A1 | 4/2005 | King | 165/163 |
| 2005/0097988 A1 | 5/2005 | Kodas et al. | 75/332 |
| 2005/0199739 A1 | 9/2005 | Kuroda et al. | |
| 2005/0220695 A1 | 10/2005 | Abatzoglou et al. | |
| 2005/0233380 A1 | 10/2005 | Pesiri et al. | 435/7.1 |
| 2005/0240069 A1 | 10/2005 | Polverejan et al. | 585/444 |
| 2005/0258766 A1 | 11/2005 | Kim | 315/111.21 |
| 2006/0051505 A1* | 3/2006 | Kortshagen et al. | 427/212 |
| 2006/0068989 A1 | 3/2006 | Ninomiya et al. | |
| 2006/0094595 A1 | 5/2006 | Labarge | |
| 2006/0096393 A1 | 5/2006 | Pesiri | 73/863.21 |
| 2006/0105910 A1 | 5/2006 | Zhou et al. | |
| 2006/0108332 A1 | 5/2006 | Belashchenko | 219/121.47 |
| 2006/0153728 A1 | 7/2006 | Schoenung et al. | |
| 2006/0153765 A1 | 7/2006 | Pham-Huu et al. | |
| 2006/0159596 A1* | 7/2006 | De La Veaux et al. | 422/151 |
| 2006/0231525 A1 | 10/2006 | Asakawa et al. | 216/56 |
| 2007/0048206 A1* | 3/2007 | Hung et al. | 423/335 |
| 2007/0063364 A1* | 3/2007 | Hsiao et al. | 264/5 |
| 2007/0084308 A1 | 4/2007 | Nakamura et al. | 75/346 |
| 2007/0084834 A1 | 4/2007 | Hanus et al. | 219/121.5 |
| 2007/0087934 A1 | 4/2007 | R.M. Martens et al. | 502/214 |
| 2007/0173403 A1 | 7/2007 | Koike et al. | |
| 2007/0253874 A1* | 11/2007 | Foret | 422/186.07 |
| 2007/0292321 A1 | 12/2007 | Plischke et al. | |
| 2008/0031806 A1 | 2/2008 | Gavenonis et al. | |
| 2008/0038578 A1 | 2/2008 | Li | |
| 2008/0064769 A1 | 3/2008 | Sato et al. | |
| 2008/0105083 A1* | 5/2008 | Nakamura et al. | 75/255 |
| 2008/0116178 A1 | 5/2008 | Weidman | |
| 2008/0206562 A1 | 8/2008 | Stucky et al. | |
| 2008/0207858 A1 | 8/2008 | Kowaleski et al. | |
| 2008/0274344 A1 | 11/2008 | Vieth et al. | |
| 2009/0010801 A1 | 1/2009 | Murphy et al. | |
| 2009/0088585 A1 | 4/2009 | Schammel et al. | |
| 2009/0114568 A1 | 5/2009 | Trevino et al. | |
| 2009/0162991 A1 | 6/2009 | Beneyton et al. | |
| 2009/0168506 A1 | 7/2009 | Han et al. | |
| 2009/0181474 A1 | 7/2009 | Nagai | |
| 2009/0274903 A1 | 11/2009 | Addiego | |
| 2009/0286899 A1 | 11/2009 | Hofmann et al. | |

FOREIGN PATENT DOCUMENTS

| | | |
|---|---|---|
| JP | 56146804 A * | 11/1981 |
| JP | 7031873 A | 2/1995 |
| WO | WO 02/092503 | 11/2002 |
| WO | 2004052778 A2 | 6/2004 |
| WO | WO 2006/0679213 A1 | 8/2006 |
| WO | WO 2006079213 A1 * | 8/2006 |

OTHER PUBLICATIONS

National Aeronautics and Space Administration, "Enthalpy", http://wwww.grc.nasa.gov/WWW/K-12/airplane/enthalpy.html, Nov. 23, 2009, 1 page.

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I Ii, P. Fauchais, Universite de Limoges, 123 Avenue A. Thomas 87000, Limoges, F. , Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M. Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier..

* cited by examiner

SHAPE OF CONE AND AIR INPUT ANNULUS

CROSS-REFERENCE TO RELATED APPLICATIONS

The present application claims priority to U.S. Provisional Application Ser. No. 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

Gas or vapor phase particle production is an important technique for producing engineered materials, especially nano-materials. The present invention relates to methods of cooling, collecting and controlling the flow of a reactive medium containing gas or vapor phase particles.

BACKGROUND OF THE INVENTION

Specific characteristics of particles produced in gas or vapor phase synthesis reactions depend not only on the energy delivered to the reactive medium, but also on the conditioning of the reactive medium once the medium has left the energy delivery zone.

In a particle producing reactor, basic product species are formed within extremely short time spans following ejection of a hot, reactive medium from the energy deliver zone. Following ejection, further formation mechanisms determine the ultimate characteristics of the final product.

Although chemical reactions such as nucleation and surface growth within precursor materials occur largely during energy delivery, these formation mechanisms continue to be active in the first short moments following ejection. More prevalent in the post-ejection time period are bulk formation mechanisms such as coagulation and coalescence, which operate on already formed particles. Any proper conditioning of the hot, reactive medium following ejection from the energy delivery zone must account for these and other formation mechanisms to form a final product having desired characteristics.

In addition to particle formation, proper conditioning must account for post-formation processing of the product. Although particles, once formed, cool rapidly through radiative heat loss, the residual gas in which they are entrained after formation cools much more slowly, and especially so when confined. Confinement is necessary to some degree in any controlled-environment processing system, and economic concerns usually dictate relatively small, confining controlled environments. Therefore, such systems must provide efficient mechanisms for cooling of the entire gas-particle product, yet also provide for efficient transport of the product to collection points within the system.

The transportation of particles within a gas stream relies on entrainment of the particles, which is largely a function of particle properties, e.g., mass, temperature, density, and inter-particle reactivity, as well as gas properties, e.g., density, velocity, temperature, density, viscosity, and composite properties, such as particle-gas reactivity. Cooling of a gas by definition affects gas temperature, but also may easily lead to changes in other properties listed above, exclusive of mass. In view of this, balancing efficient cooling and transport of gas-particle product requires careful optimization of process parameters, which the present invention seeks to achieve.

SUMMARY OF THE INVENTION

According to the present invention, a gas and vapor conditioning system is presented. The conditioning system is primarily intended to condition reactive gas-vapor product within gas phase particle production reactors, such as flame reactors, plasma reactors, hot wall reactors and laser reactors. Conditioning performed within the system includes the collection, cooling and delivery of reactive gas-vapor mixtures for collection or sampling and accounts for particle formation and interaction mechanisms within the reactive gas-vapor mixture.

The conditioning system comprises a constricting chamber preferably having a circular cross section and a first end with a first diameter, and a second end with a second diameter, wherein the first diameter is larger than the second diameter, and having an interior surface forming smoothly varying constrictions from the first end to the second end. The first end is coupled with a cover, which includes an injection port coupled to a reactive gas-vapor injection device. This coupling is preferably air tight, and maintained with silicone paste or some other heat resistant insulating material. Preferably, one or more supply ports are formed within and arranged circumferentially in an annulus on the cover. In alternative embodiments, there need not be any supply ports on the cover, but instead, one or more supply ports can be arranged circumferentially elsewhere in the constricting chamber. The second end is coupled with an ejection port having a diameter equal to the second diameter. It is contemplated that the constricting chamber can have a cross section of any shape, including rectangular, oval, and irregular shapes.

The gas and vapor conditioning system works to collect, cool, deliver and further condition a reactive gas-vapor mixture flowing from an energy delivery zone within a gas phase particle production reactor. In operation, once a hot, reactive gas mixture flows into the constricting chamber, it rapidly expands and flows towards the second end of the chamber. Several factors are responsible for this the direction of gas flow. The gas supply process is preferably continuous, at least during each production period, forcing the gas-vapor mixture toward the second end of the constricting chamber. Furthermore, the gas mixture already tends to flow in this direction due to inertia of the gas mixture flowing through and from the energy delivery zone. Although these two reasons tend to bias flow from the first end to the second end during operation, the preferred configuration of the present invention drives flow in this direction using more active means. Preferably, a vacuum configured to form a negative pressure gradient within the constricting chamber forces flow of the gas-particle mixture form the first end to the second end.

Furthermore, and as already alluded to above, the gas-vapor mixture tends to expand within the constricting chamber because temperatures and pressures in the energy delivery zone exceed those within the constricting chamber. Although this expansion is desirable and necessary to some extent for cooling and for proper conditioning of the mixture, it also has consequences which must be mitigated. Expansion of the mixture gas against the inner surfaces of the constricting chamber can lead to adhesion thereto by particles within the gas and subsequently to the depositing of residues within the chamber. This pollution of the chamber will affect fluid flow within the chamber, and ultimately decrease process control, and possibly even contaminate the output. The occurrence of significant deposits would therefore necessitate regular cleaning of the chamber.

However, the occurrence of residue is minimized by the present invention, in which conditioning fluid flows through the one or more supply ports and along the inner surface of the constricting chamber, thereby providing a sheath of conditioning fluid between the gas-vapor mixture and the surface of the constricting chamber. In a preferred embodiment, the conditioning fluid is provided at a substantially cooler temperature than that of the gas-vapor mixture. Furthermore, the flow rate of the conditioning fluid is preferably substantially higher than that of the gas-vapor mixture. This disparity in flow rates allows for expansion of the gas-vapor mixture against the sheath of conditioning fluid and, to a certain degree, intermixture of the two fluids. However, the density and higher flow rate of the conditioning fluid substantially prevents the gas-vapor mixture from encountering the inner surfaces of the chamber. The composition of the conditioning fluid is determined partially with deference to the specific product being synthesized. Typically, the conditioning fluid is an inert gas, such as argon, neon or helium. Argon is preferred due to its higher molecular weight. Preferably, the conditioning fluid is supplied passively, as described more fully below, through a neutral pressure controlled atmosphere environment formed around the plurality of ports within the cover.

Furthermore, as described above, condensation of particles within the gas-vapor occurs rapidly upon flowing into the chamber and continues as the mixture flows through the chamber. These particles experience rapid radiative heat loss, as was also mentioned above. A certain amount of this radiation is absorbed by the conditioning fluid. However, as will be more fully explained below, a much larger fraction of the radiation is absorbed and dissipated by the chamber surfaces. More importantly, although the low flow rates of the mixture alone may be unable to maintain entrainment of newly formed particles, the high flow rates of conditioning fluid along the inner surfaces of the chamber and the constriction of the chamber and attendant confinement of the gas flow as it moves toward the second end of the chamber act together to maintain entrainment of all but the largest agglomerations of particles. This loss of large agglomerations from the gas flow system is desirable, and although it will still result in some contamination of the chamber, its occurrence is engineered into the system and minimized.

In the preferred embodiments, the conditioning fluid flow enters the constricting chamber near the first end and provides a sheath along substantially the entire inner surface of the constricting chamber. However, in alternative embodiments the supply ports are positioned between the first end and second ends of the constricting chamber and provide a sheath of conditioning gas only along a portion of the inner surface of the constricting chamber. This configuration can allow certain temperature-dependent formation mechanisms within the reactive gas-vapor to occur for selected periods of time prior to cooling of the gas-vapor, permitting formation of products having production mechanisms of variable time lengths.

Therefore, the present invention provides a high flow sheath of conditioning fluid along the inner walls of a constricting chamber into which a hot gas-vapor mixture flows, forming particles. As the conditioning fluid and the gas-particle mixture flow through the constricting chamber to the ejection port on the second end thereof, the smoothly varying constrictions and differential in temperature and flow rate between the gas-particle mixture and the conditioning fluid act to maintain entrainment of the particles and to cool the hot gas mixture.

In one aspect of the present invention, a constricting chamber is provided having a first end and a second end opposite the first end. The constricting chamber comprises an interior surface formed between the first end and the second end. The interior surface is disposed circumferentially around and defines an interior space and a longitudinal axis of the constricting chamber. A frusto-conical surface is formed from the interior surface. The frusto-conical surface narrows as it extends away from the first end and into the second end. An ejection port is disposed at the second end of the constricting chamber. The ejection port is substantially aligned with the longitudinal axis. A cover is disposed at the first end of the constricting chamber. The cover is substantially perpendicular to the longitudinal axis and comprises a center substantially aligned with the longitudinal axis. A reactive mixture injection port is disposed on the cover proximate the center of the cover. The reactive mixture injection port is configured to receive a reactive mixture into the constricting chamber. An annular supply portion is disposed circumferentially around the longitudinal axis. The annular supply portion comprises one or more supply ports configured to supply conditioning fluid into the constricting chamber in an annular formation along the interior surface.

In another aspect of the present invention, a particle production system is provided. The particle production system comprises an energy supply device having an energy delivery zone. The energy supply device is configured to produce a reactive mixture within the energy delivery zone. The particle production system also comprises a constricting chamber having a first end, a second end opposite the first end, and an interior surface formed between the first end and the second end. The interior surface is disposed circumferentially around and defines an interior space and a longitudinal axis of the constricting chamber. A frusto-conical surface is formed from the interior surface and narrows as it extends away from the first end and into the second end. An ejection port is disposed at the second end of the constricting chamber in substantially alignment with the longitudinal axis. A cover is disposed at the first end of the constricting chamber. The cover is disposed in a position substantially perpendicular to the longitudinal axis of the constricting chamber. The cover comprises a center substantially aligned with the longitudinal axis. A reactive mixture injection port is disposed on the cover proximate the center and is configured to receive the reactive mixture into the constricting chamber from the energy delivery zone. An annular supply portion is disposed circumferentially around the longitudinal axis. The annular supply portion comprises one or more supply ports configured to supply conditioning fluid into the constricting chamber in an annular formation along the interior surface of the constricting chamber.

In yet another aspect of the present invention, a method of conditioning a reactive mixture is provided. The method comprises providing a constricting chamber having a first end, a second end opposite the first end, and an interior surface formed between the first end and the second end. The interior surface is disposed circumferentially around and defines an interior space and a longitudinal axis of the constricting chamber. A frusto-conical surface is formed from the interior surface and narrows as it extends away from the first end and into the second end. A cover is disposed at the first end of the constricting chamber in a position substantially perpendicular to the longitudinal axis of the constricting chamber. The cover comprises a center that is substantially aligned with the longitudinal axis. A reactive mixture flows into the interior space of the constricting chamber through a reactive mixture injection port that is disposed on the cover of the constricting chamber proximate the center. A conditioning fluid flows into the interior space of the constricting chamber through an annular supply portion in an annular formation along the interior surface of the constricting chamber. The annular supply portion comprises one or more supply ports disposed circumferentially around the longitudinal axis of the constricting chamber. The reactive mixture is cooled within the interior space of the constricting chamber, thereby forming a cooled mixture. The cooled mixture flows through an ejection port disposed at the second end of the constricting chamber. The ejection port is substantially aligned with the longitudinal axis of the constricting chamber.

DETAILED DESCRIPTION OF THE INVENTION

Figure 1:
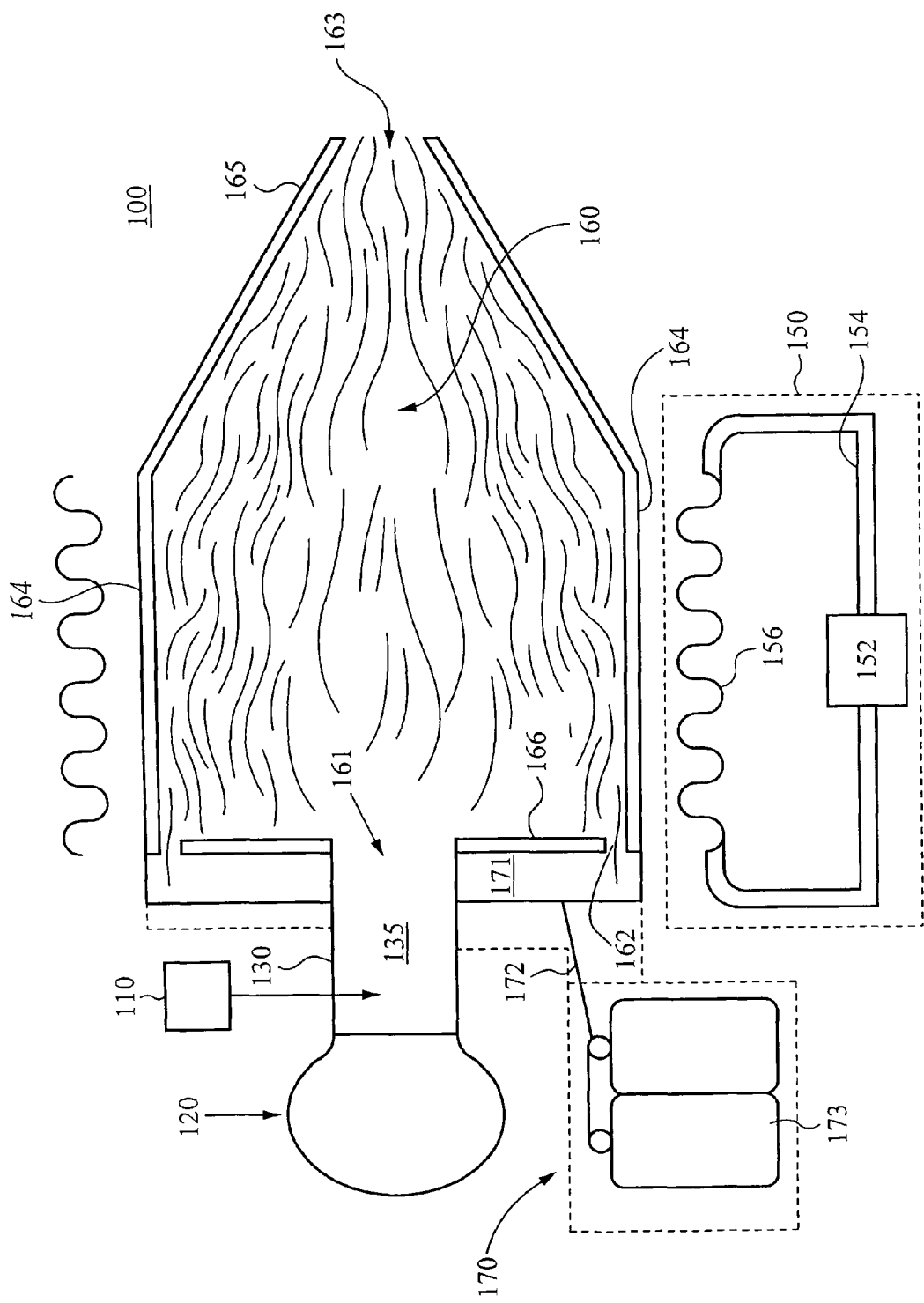
FIG. 1 is a cross-sectional view of one embodiment of a nano-particle production system in accordance with the principles of the present invention.

The description below concerns several embodiments of the invention. The discussion references the illustrated preferred embodiment. However, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders(nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

Preferably, the dimensions of the constricting chamber of the present invention have the following general relationships: the diameter of the first end is substantially greater than that of the injection port, the diameters of the one or more supply ports are substantially smaller than that of the injection port, the diameter of the second end of the constricting chamber is substantially smaller than the first diameter and on the order of the diameter of the injection port. Additionally, because of the inclusion of the annulus of smaller ports, the diameter of the injection port is necessarily smaller than that of the first end of the constricting chamber. Furthermore, the combined surface area of the smaller ports is preferably equal to the surface area of the ejection port, though substantial equality or substantial dissimilarity are also contemplated. More specifically, the constricting chamber preferably has a first dimension of approximately 12 inches, constricting to a second dimension of approximately two inches over a distance of 24 inches. Preferred aspect ratios, i.e., ratios of the first diameter to the distance between the first and second ends, range between one to three and one to two.

As mentioned above, the ejection port and combined one or more supply ports preferably have substantially equal surface areas. In an alternative embodiment, the one or more supply ports have variable combined surface area, but are capable of achieving a combined surface area of substantial equality to the ejection port. The equality, or substantial equality, of surface areas between the one or more supply ports and the ejection outlet is preferred to minimize the pressure drop within the chamber, and to minimize compression of the conditioning fluid as it flows from the ejection port. Flow of the conditioning fluid into the one or more supply ports is preferably caused by formation of a negative pressure differential with the ejection outlet, which also aids in maintaining flow of the mixture through the chamber. This negative pressure differential is preferably formed by fluidly coupling a vacuum formation system with the ejection port. In alternative embodiments, active injection of conditioning fluid is contemplated, but this scheme has many disadvantages when compared to passively drawing conditioning fluid into the system by vacuum.

Because the present invention preferably uses a pressure differential to motivate flow of the conditioning fluid through the one or more supply ports, variation of the combined surface area of the one or more supply ports allows variation of the flow rate of conditioning fluid. As described below, in some configurations a difference in flow rates between the conditioning fluid sheath and the reactive gas vapor contributes to a conditioning effect of the fluid. Therefore, adjustment of the flow rate of the conditioning fluid permits optimization of the conditioning effect that a flow rate differential provides.

Within the present invention, many configurations of the smoothly varying constrictions are contemplated. In the preferred embodiments, these constrictions will smoothly vary in such a way so as to accelerate fluid flow and provide a Venturi-effect pressure differential within the chamber. In general, the constriction shape is determined while accounting for several factors affecting the conditioning of the reactive gas-vapor. Two factors are of major concern. First, adequate space must be provided within the region proximal to the first end of the constricting chamber to accommodate rapid expansion of the hot gas-vapor following its flowing into the chamber. Second, constriction of the chamber within the region proximal to the second end of the constricting chamber must not occur so rapidly that undue turbulence is introduced into the gas-vapor as it flows to the ejection port. For any chamber having fixed length between the first and second ends, these requirements present contradictory design concerns. However, the several embodiments of the present invention include designs which accommodate both concerns.

In the preferred configuration for constrictions within the constricting chamber, a cylindrical surface of substantially constant interior diameter extends from the first end toward the second end of the chamber until, at a point of sufficient distance from the second end to allow a smooth constriction, the surface constricts in a cone like shape to the ejection port at the second end. In alternative embodiments, a cone like surface constricts, at a constant rate or otherwise, from the first end to the ejection port at the second end. In still further embodiments, the surface constricts to a minimum diameter at a point between the first and second ends. The minimum diameter may be less than or equal to the second diameter, which is also the diameter of the ejection port. Where the minimum diameter is less than the second diameter, the surface smoothly varies to open at the second diameter. Where the minimum diameter is equal to the second diameter, the surface extends in a cylinder-like surface to meet the ejection port. Other types of smooth variations are also considered, so long as they effectively balance the design concerns described above in a manner consistent with the present invention.

The constricting chamber of the present invention preferably comprises a thin shell. The exterior of the constricting chamber is preferably cooled by a fluid cooling system, to dissipate heat absorbed into the body of the constricting chamber from the gas particle mixture. As mentioned above, this heat will primarily be supplied to the constricting chamber body in the form of radiation from the newly formed particles as the rapidly cool within the constricting chamber. In order to avoid overheating of the chamber body, the fluid cooling system is preferably included.

Furthermore, although the embodiments discussed above have described only the injection and ejection ports and the one or more supply ports, in some configurations the inclusion of additional ports within the constricting chamber is preferred. Depending on the configuration of the constrictions within the chamber, separation of the hot gas particle mixture from the conditioning fluid will begin to break down prior to passage through the ejection port without further introduction of conditioning fluid. Preferably, constrictions are configured so that this does not occur. However, if constriction configurations that would otherwise lead to such break down are deemed necessary, inclusion of auxiliary ports is preferred. These auxiliary ports are preferably placed in a constricting area of the chamber, and arranged or otherwise configured to minimally disturb gas flow within the constricting area of the chamber. Use of the vacuum systems, as mentioned above, combined with the preferable inducement of Venturi effect pressure differentials within the constricting chamber, combine to draw conditioning fluid through the auxiliary ports at the optimal rate necessary to maintain entrainment of particles and separation of the hot gas-particle mixture from the conditioning fluid.

Referring now to FIG. 1, a gas phase particle production system 100 is provided. The System 100 comprises a precursor supply device 110 and a working gas supply device 120 each fluidly coupled to an energy supply device 130 having an energy delivery zone 135 therein. The energy supply device 130 is fluidly coupled with an injection port 161 of a constricting chamber 160, thereby allowing the energy delivery zone 135 to fluidly communicate with the interior space of the constricting chamber 160. An annular supply portion 162, comprising one or more supply ports, also allows fluid communication of the chamber 160 with a controlled atmosphere system 170. The constricting chamber 160 is also fluidly coupled with an ejection port 163.

Generally, the system 100 operates as a reactor, producing an output comprising particles entrained within a gas stream. Production includes the basic steps of combination, reaction, and conditioning. The system combines precursor material, such as powder, supplied from the precursor supply device 110 and working gas, such as a mixture of hydrogen gas and argon gas, supplied from the working gas supply device 120 within the energy delivery zone 135 to form an energized, reactive mixture. The mixture comprises one or more materials in a plurality of phases, which may include vapor, gas, and plasma.

Some embodiments of the present invention revolve around the use of a nano-powder production reactor. In general, vapor phase nano-powder production means are preferred. The embodiments of the present invention can use elements of nano-powder production systems similar to those disclosed in U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas.

Referring back to FIG. 1, the reactive mixture flows from the energy delivery zone 135 into the constricting chamber 160 through the injection port 161. As the hot mixture moves from the energy delivery zone 135, it expands rapidly within the chamber 160 and cools. While the mixture flows into the chamber 160, the annular supply port 162 supplies conditioning fluid along the inner surfaces of the chamber 160. The conditioning fluid combines, at least to some extent, with the mixture, and flows from the chamber 160 through the ejection port 163.

As previously described in more detail, during a brief period immediately after entering the chamber 160, particle formation occurs. Furthermore, the supply of conditioning fluid along the inner surfaces of the chamber 160 works to condition the mixture and to maintain entrainment of the particles therein. This supply of conditioning fluid also works to prevent deposit of material on the inner surfaces of the chamber 160, preferably by creating a protective sheath separating particles from the inner surface of the chamber 160.

Still referring to FIG. 1, the structure of the chamber 160 is preferably formed of relatively thin walled components capable of dissipating substantial quantities of heat. For example, the thin-walled components can conduct heat from inside the chamber and radiate the heat to the ambient. The chamber 160 comprises a substantially cylindrical surface 164, a cone-like surface 165, and an annular surface 166 connecting the injection port 161 with the cylindrical surface 164. The annular surface 166 provides a cover for one side of the chamber 160. The cylindrical surface 164, having a large diameter relative to the size of the injection port 161, provides accommodation for the expansion of the mixture that occurs after it flows into the chamber 160. The cone-like surface 165 is sufficiently smoothly varying so as to not unduly compress fluid flowing from through the chamber 160 to the ejection port 163.

As described above, substantial heat is emitted, mostly in the form of radiation, from the mixture following its entry into the chamber 160. The chamber 160 is preferably designed to dissipate this heat efficiently. Hence, the surfaces of the chamber 160 are preferably exposed to a cooling apparatus. As illustrated, the cone-like surface 163 and the cylindrical surface 164 are exposed to the cooling apparatus 150. In other embodiments, other portions of the structure are exposed to the cooling apparatus 150.

The cooling apparatus 150 preferably comprises the heat exchanger 156 fluidly coupled with the heat dissipation device 152. However, other configurations of a cooling apparatus are contemplated.

Still referring to FIG. 1, the controlled atmosphere system 170 comprises the chamber 171 into which conditioning fluid is introduced from one or more reservoirs 173 through a conduit 172. As described above, the conditioning fluid preferably comprises argon. However, other inert, relatively heavy gases are equally preferred. Also as discussed above, the preferable mechanism of providing the conditioning fluid into the chamber 160 is the formation of a pressure differential between the chamber 160 and the outlet 163. Such pressure differential will draw the conditioning fluid into the chamber 160 through the ports 162. Other, less preferred, methods of providing the conditioning fluid include forming positive pressure within the chamber 171.

The constricting chamber 160 has a longitudinal axis that runs from the injection port 145 to the ejection port 163. In a preferred embodiment, the injection port 161 is disposed proximate the center of the annular surface 166, the ejection port 163 is disposed proximate the center of the opposite end of the constricting chamber 160, and both the injection port 161 and the ejection port 163 are substantially aligned with the longitudinal axis of the constricting chamber 160.

Figure 2A:
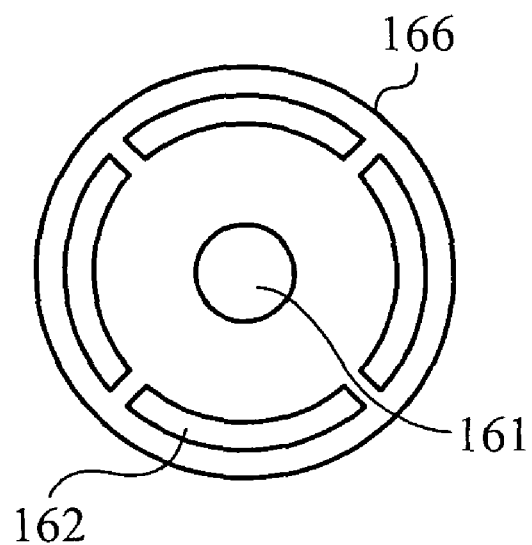
FIGS. 2A and 2B are axial views of different embodiments of an annular surface in accordance with the principles of the present invention.

Referring now to FIG. 2A, the annular surface 166 comprises a plurality of supply ports 162. The injection port 161 is preferably positioned in the center of the annular surface 166 and has a perpendicular orientation relative to the surface. The supply ports 162 are arranged in an annular fashion around the perimeter of the annular surface 166. As previously described with reference to FIG. 1, the supply ports communicate with the chamber 160. Preferably, the ports are oriented to direct flow along the inner surfaces of the chamber 160. In one embodiment, the Ports are oriented perpendicularly within the annular surface 166 and mounted flush to the interior surfaces of the chamber 160. In an alternative embodiment, the ports are slightly angled relative to the perpendicular with respect to the annular surface 166 so as to direct fluid more directly against, along, or away from the inner surfaces of the chamber 160.

Figure 2B:
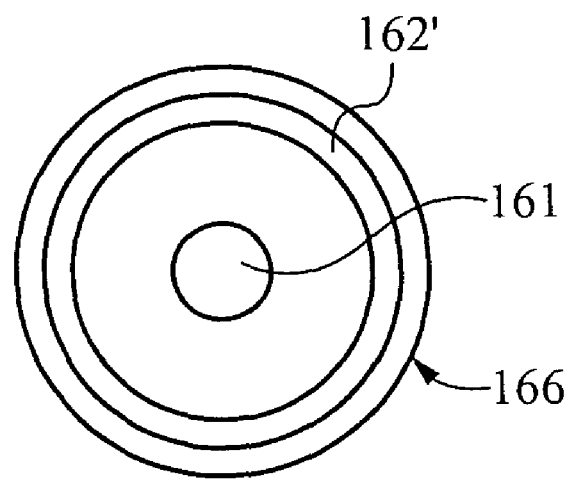
Figure 3:
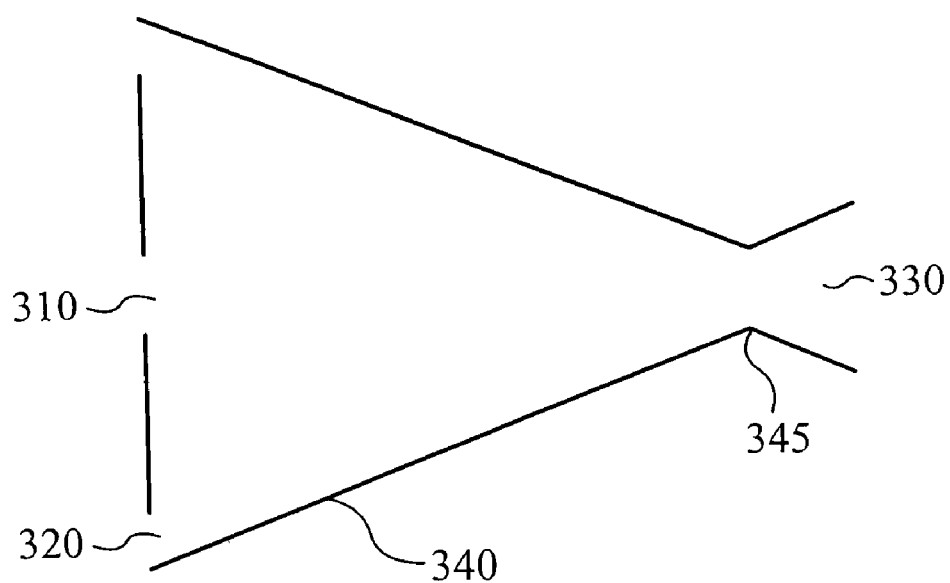
FIG. 3 is a cross-sectional view of an alternative embodiment of a constricting chamber in accordance with the principles of the present invention.
Figure 4:
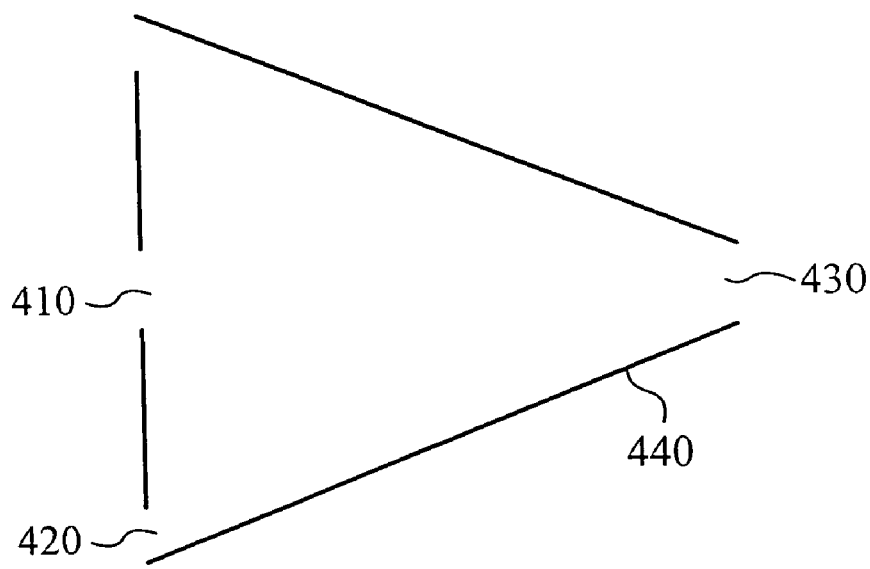
FIG. 4 is a cross-sectional view of another alternative embodiment of a constricting chamber in accordance with the principles of the present invention.
Figure 5:
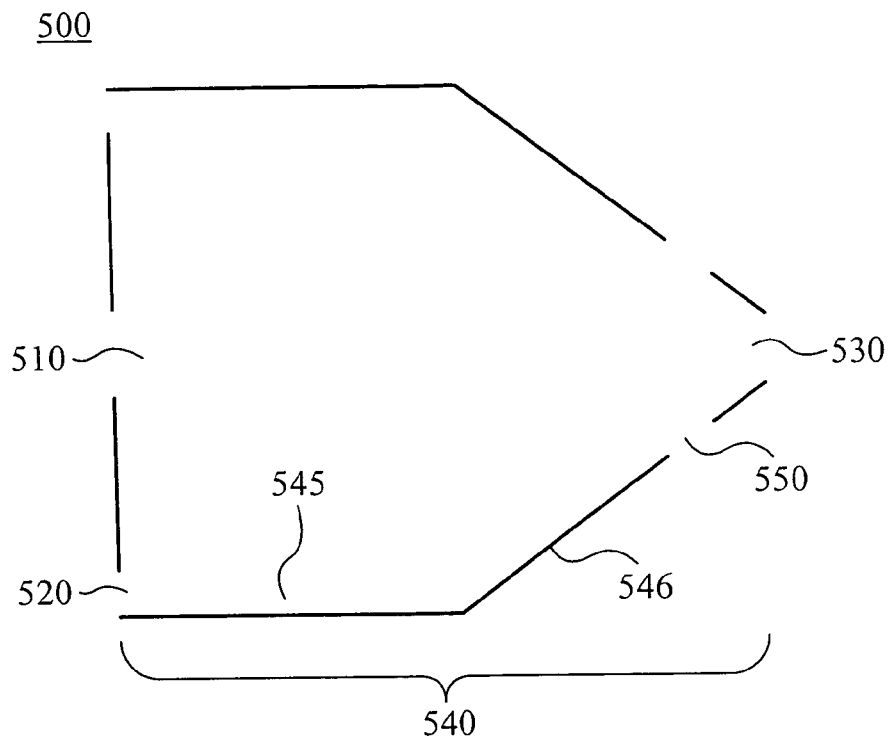
FIG. 5 is a cross-sectional view of yet another alternative embodiment of a constricting chamber in accordance with the principles of the present invention.

Referring now to FIG. 2B, the annular surface 166 comprises one continuous annular Supply port 162'. The injection port 161 is preferably positioned in the center of the annular surface 166 and has a perpendicular orientation relative to the surface. The annular supply port 162' is configured to lie around the perimeter of the annular surface 166. As previously described with reference to FIG. 1, the port communicates with the chamber 160. Preferably, the port is oriented to direct flow along the inner surfaces of the chamber 160. In one embodiment, the ports is oriented perpendicularly within the annular surface 166 and mounted flush to the interior surfaces of the chamber 160. In an alternative embodiment, the port is slightly angled relative to the perpendicular with respect to the annular surface 166 so as to direct fluid more directly against, or away from, the inner surfaces of the chamber 160.

Although the port 162' and ports 162 illustrated within FIGS. 2A and 2B have fixed size, alternative embodiments include port structures with variable total area. Because the port structures deliver fluid motivated by a pressure differential between the fluid source and the chamber, adjusting the total area of the port structures changes the rate at which fluid flows into the chamber.

Referring now to FIGS. 3 through 6, various embodiments of the constricting chamber as employed in the present invention are discussed. The constricting chamber 300 includes injection port 310, ejection port 330 and one or more supply ports 320. Fluid moving from the injection port through the chamber 300 initially expands into the wider end of the cone-like shape formed by frusto-conical surface 340. Fluid moving through the chamber 300 is constricted as the surface 340 narrows, reaching an apex 345, at which fluid is maximally constricted. The smooth constrictions of the surface 340 form a Venturi which introduces a pressure differential in the moving fluid, further encouraging flow from the injection port 310 to the ejection port 330. Furthermore, particle-containing-fluid flowing through the injection port 310 is entrained with fluid flowing through the smaller ports 320 as the fluids move together through the chamber 340.

The constricting chamber 400 includes injection port 410, ejection port 430 and one or more supply ports 420. Fluid moving from the injection port through the chamber 400 initially expands into the wider end of the cone-like shape formed by frusto-conical surface 440. Fluid moving through the chamber 400 is constricted as the surface 440 narrows, reaching an apex at the ejection port 430, at which fluid is maximally constricted. The smooth constrictions of the surface 440 constrict the flow of gas through the chamber 400. Depending on the configuration of chamber or conduit attached with the ejection port 430, a Venturi may be formed. Furthermore, particle-containing-fluid flowing through the injection port 410 is entrained with fluid flowing through the smaller ports 420 as the fluids move together through the chamber 440.

The constricting chamber 500 includes injection port 510, ejection port 530, one or more supply ports 520, and one or more auxiliary ports 550. Fluid moving from the injection port 510 through the chamber 500 initially expands into the cylindrical portion of the chamber 500 formed by cylindrical surface 545. Fluid moving through the chamber 500 is eventually constricted as it enters the cone-shaped portion of the chamber 500 formed by the frusto-conical surface 546. The space within the surface 546 narrows, reaching an apex at the ejection port 530, at which fluid is maximally constricted. The smooth constrictions of the surface 546 constrict the flow of gas through the chamber 500. Depending on the configuration of chamber or conduit attached with the ejection port 530, a Venturi may be formed. Furthermore, particle-containing-fluid flowing through the injection port 510 is entrained with fluid flowing through the smaller ports 520 as the fluids move together through the chamber 540. The auxiliary ports 550 provide additional conditioning fluid as constriction occurs. As discussed above, in the preferred system, conditioning fluid is drawn into the ports 520 and 550 and is supplied at the correct rate to maintain entrainment.

Figure 6:
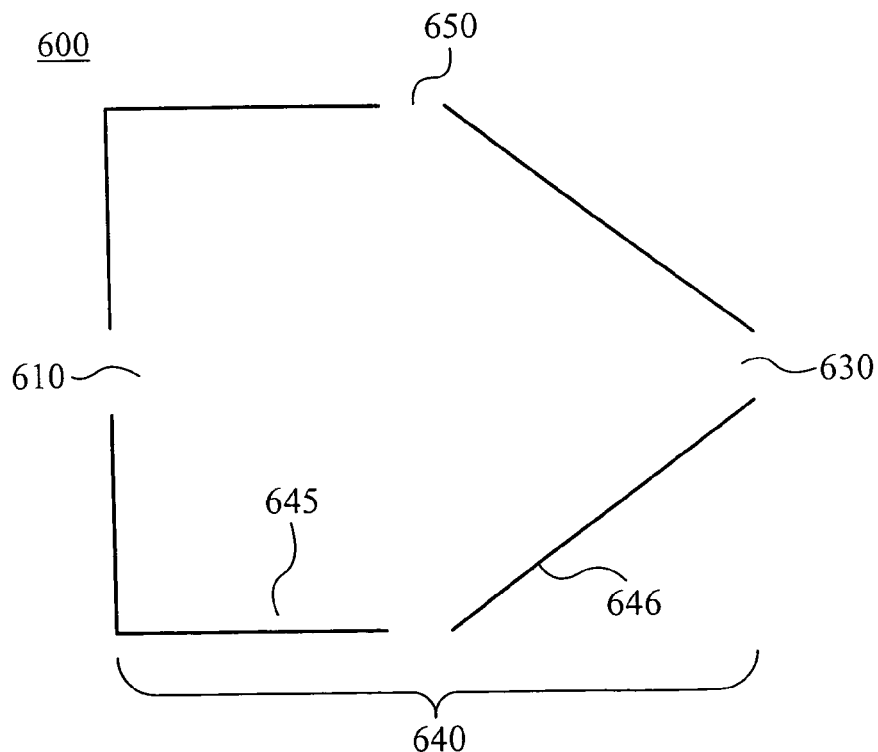
FIG. 6 is a cross-sectional view of still another alternative embodiment of a constricting chamber in accordance with the principles of the present invention.

Referring now to FIG. 6, the constricting chamber 600 includes injection port 610, ejection port 630, and one or more supply ports 650. Fluid moving from the injection port 610 through the chamber 600 initially expands into the cylindrical portion of the chamber 600 formed by cylindrical surface 645. Fluid moving through the chamber 600 is eventually constricted as it enters the cone-shaped portion of the chamber 600 formed by the frusto-conical surface 646. The space within the surface 646 narrows, reaching an apex at the ejection port 630, at which fluid is maximally constricted. The smooth constrictions of the surface 646 constrict the flow of gas through the chamber 600. Depending on the configuration of chamber or conduit attached with the ejection port 630, a Venturi may be formed. Furthermore, once particle-containing-fluid flowing through the injection port 610 has expanded as it moves through the first part of the chamber formed by the surfaces 645, it joins with fluid flowing through the one or more supply ports 650 as the fluids move together through the chamber 640. As discussed above, in the preferred system, conditioning fluid is drawn into the ports 650 and is supplied at the correct rate to maintain entrainment.

Figure 7:
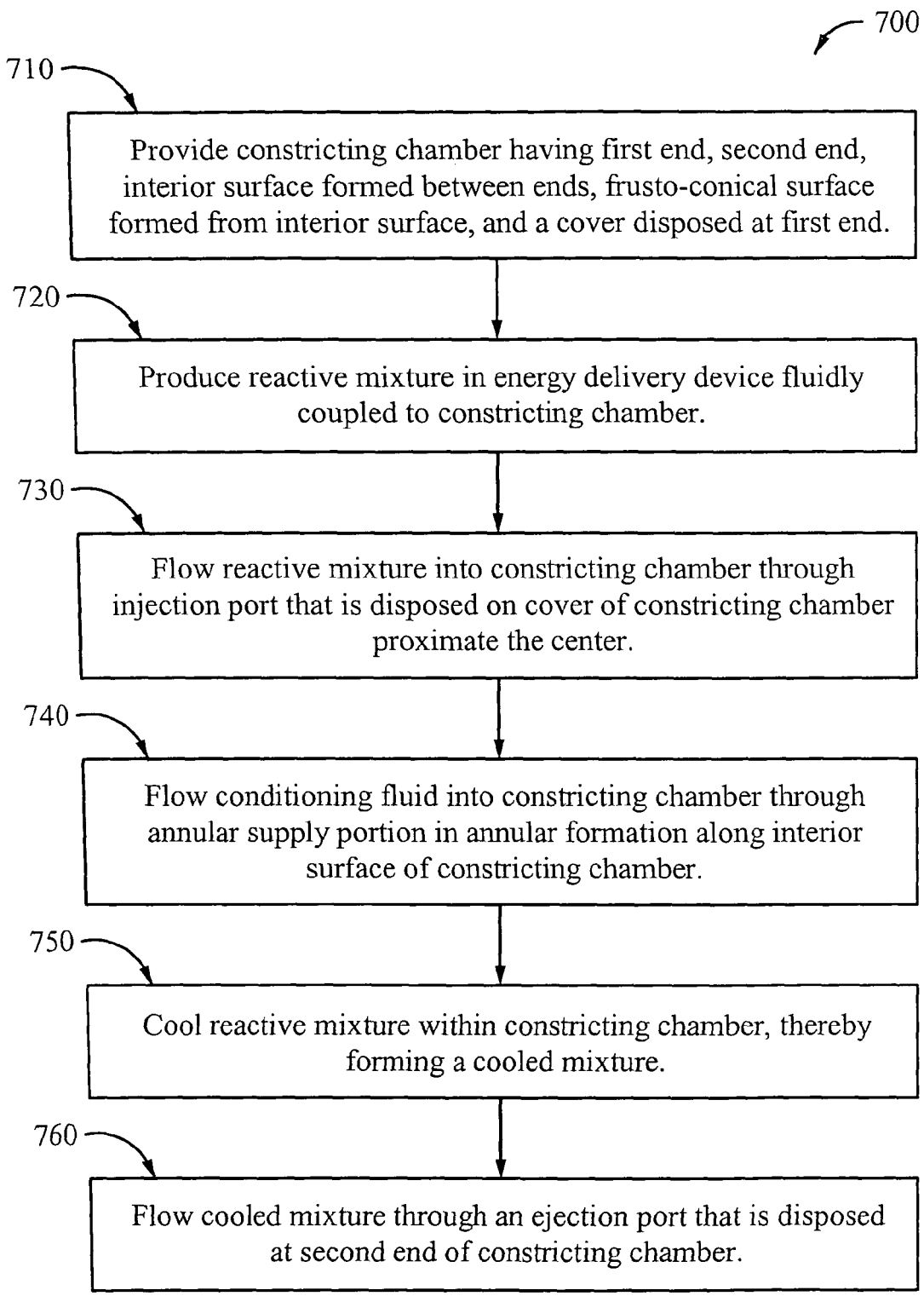
FIG. 7 is a flowchart illustrating one embodiment of a method for conditioning a reactive mixture in accordance with the principles of the present invention.

FIG. 7 is a flowchart illustrating one embodiment of a method 700 for conditioning a reactive mixture in accordance with the principles of the present invention. As would be appreciated by those of ordinary skill in the art, the protocols, processes, and procedures described herein may be repeated continuously or as often as necessary to satisfy the needs described herein. Additionally, although the steps of method 700 are shown in a specific order, certain steps may occur simultaneously or in a different order than is illustrated. Accordingly, the method steps of the present invention should not be limited to any particular order unless either explicitly or implicitly stated in the claims.

At step 710, a constricting chamber is provided consistent with the principles of the present invention discussed above. The constricting chamber has a first end, a second end opposite the first end, and an interior surface formed between the first end and the second end. The interior surface is disposed circumferentially around an interior space and a longitudinal axis of the constricting chamber, thereby defining the interior space and the longitudinal axis of the constricting chamber. The constricting chamber also comprises a frusto-conical surface formed from the interior surface. The frusto-conical surface narrows as it extends away from the first end and into the second end. The constricting chamber further includes a cover disposed at the first end of the constricting chamber. The cover is disposed in a position substantially perpendicular to the longitudinal axis. Additionally, the cover comprises a center that is Substantially aligned with the longitudinal axis of the constricting chamber.

At step 720, an energy delivery device, which is fluidly coupled to the interior space of the constricting chamber, produces a reactive mixture. It is contemplated that the reactive mixture can be produced in a variety of ways. However, in a preferred embodiment, the energy supply device receives a working gas from a working gas supply device, delivers energy to the working gas to form a plasma stream, receives a precursor material from a precursor supply device, and applies the plasma stream to the precursor material, thereby vaporizing the precursor material and forming the reactive mixture. The reactive mixture preferably comprises vaporized precursor material entrained within the plasma stream.

At step 730, the reactive mixture flows into the interior space of the constricting chamber through a reactive mixture injection port disposed on the cover of the constricting chamber. The injection port is preferably disposed proximate the center of the cover so that it is substantially aligned with the longitudinal axis of the constricting chamber.

At step 740, a conditioning fluid flows into the interior space of the constricting chamber through an annular supply portion in an annular formation along the interior surface of the constricting chamber. The annular supply portion comprises one or more supply ports disposed circumferentially around the longitudinal axis. As previously discussed, the annular portion can be disposed on the cover or along the interior surface of the constricting chamber. Furthermore, the annular supply portion can comprise a plurality of ports disposed in an annular formation or one continuous supply port disposed in an annular formation.

At step 750, the reactive mixture is cooled within the interior space of the constricting chamber, thereby forming a cooled mixture. In preferred embodiments, this cooling of the reactive mixture results in the formation of condensed particles that comprise the precursor material.

At step 760, the cooled mixture flows through an ejection port disposed at the second end of the constricting chamber. In a preferred embodiment, the ejection port is substantially aligned with the longitudinal axis of the constricting chamber.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of conditioning a reactive mixture, the method comprising:

providing a constricting chamber having a first end, a second end opposite the first end, and an interior surface formed between the first end and the second end and disposed circumferentially around and defining an interior space and a longitudinal axis of the constricting chamber, a frusto-conical surface formed from the interior surface and narrowing as it extends away from the first end and into the second end, and a cover disposed at the first end of the constricting chamber substantially perpendicular to the longitudinal axis and comprising a center substantially aligned with the longitudinal axis;

an energy supply device applying a plasma stream to a precursor material, thereby vaporizing the precursor material and forming the reactive mixture, wherein the reactive mixture comprises vaporized precursor material entrained within the plasma stream, and wherein the precursor material is provided to the energy supply device in powder form;

flowing the reactive mixture into the interior space of the constricting chamber through a reactive mixture injection port disposed on the cover of the constricting chamber proximate the center;

flowing a conditioning fluid into the interior space of the constricting chamber through an annular supply portion in an annular formation along the interior surface of the constricting chamber, wherein the annular supply portion comprises one or more supply ports disposed circumferentially around the longitudinal axis, and the annular supply portion comprises one or more supply ports disposed on the cover in an annular formation around the reactive mixture injection port and configured to supply conditioning fluid into the constricting chamber along the interior surface, wherein the annular supply portion is distinct from the reactive mixture injection port such that the conditioning fluid is supplied into the interior space of the constricting chamber through a different port than the reactive mixture, wherein the one or more supply ports disposed on the cover comprise one or more openings in a direction substantially parallel to the longitudinal axis of the constricting chamber;

cooling the reactive mixture within the interior space of the constricting chamber, thereby forming a cooled mixture; and flowing the cooled mixture through an ejection port disposed at the second end of the constricting chamber, wherein the ejection port is substantially aligned with the longitudinal axis.

2. The method of claim 1, wherein the annular supply portion comprises a plurality of supply ports disposed in an annular formation around the reactive mixture injection port and configured to supply conditioning fluid into the constricting chamber along the interior surface.

3. The method of claim 1, wherein the annular supply portion comprises one continuous supply port disposed in an annular formation around the reactive mixture injection port and configured to supply conditioning fluid into the constricting chamber along the interior surface.

4. The method of claim 1, wherein a second annular supply portion is disposed along the interior surface of the constricting chamber.

5. The method of claim 4, wherein the second annular supply portion comprises a plurality of supply ports disposed in an annular formation on the interior surface of the constricting chamber and configured to supply conditioning fluid into the constricting chamber along the interior surface.

6. The method of claim 4, wherein the second annular supply portion comprises one continuous supply port disposed in an annular formation on the interior surface of the constricting chamber and configured to supply conditioning fluid into the constricting chamber along the interior surface.

7. The method of claim 1, wherein the step of flowing the reactive mixture into the interior space of the constricting chamber is preceded by the steps of:
the energy supply device receiving a working gas from a working gas supply device;
the energy supply device delivering energy to the working gas to form the plasma stream; and
the energy supply device receiving the precursor material from a precursor supply device.

8. The method of claim 1, wherein:
the conditioning fluid flows into the constricting chamber at a cooler temperature than the temperature at which the reactive mixture flows into the constricting chamber; and
the conditioning fluid flows into the constricting chamber at a higher flow rate than the flow rate at which the reactive mixture flows into the constricting chamber.

9. The method of claim 1, wherein the conditioning fluid is an inert gas.

10. The method of claim 9, wherein the inert gas is argon.

11. The method of claim 1, wherein the one or more supply ports are mounted flush to the interior surface of the constricting chamber.

* * * * *